United States Patent [19]

Hashimoto et al.

[11] Patent Number: 5,567,755
[45] Date of Patent: Oct. 22, 1996

[54] COATING SOLUTION FOR FORMING COMPOSITE METAL OXIDE FILM AND PROCESS FOR MAKING SAME

[75] Inventors: Akira Hashimoto; Katsuya Tanitsu, both of Kanagawa, Japan

[73] Assignee: Tokyo Ohka Kogyo Co., Ltd., Kanagawa, Japan

[21] Appl. No.: 422,835

[22] Filed: Apr. 17, 1995

Related U.S. Application Data

[62] Division of Ser. No. 155,150, Nov. 22, 1993, Pat. No. 5,508,332, which is a division of Ser. No. 35,711, Mar. 23, 1993, Pat. No. 5,393,907.

[30] Foreign Application Priority Data

Mar. 24, 1992 [JP] Japan .................................. 4-113906
Aug. 27, 1992 [JP] Japan .................................. 4-269040

[51] Int. Cl.$^6$ ........................................ C08K 5/10
[52] U.S. Cl. .................. 524/317; 524/356; 524/357; 524/359; 524/386; 524/388; 524/394; 524/396; 524/397; 524/398; 524/399; 524/400; 524/413; 524/429; 524/500; 524/513
[58] Field of Search .................................. 524/357, 394, 524/396, 398, 356, 359, 317, 500, 533, 386, 388, 397, 399, 400, 413, 429

[56] References Cited

U.S. PATENT DOCUMENTS

| | | | |
|---|---|---|---|
| 3,532,708 | 10/1970 | Blance | 524/357 |
| 3,607,834 | 9/1971 | Marx et al. | 524/357 |
| 3,769,254 | 10/1973 | Anderson et al. | 524/357 X |
| 3,822,232 | 7/1974 | Huang et al. | 524/357 X |
| 3,886,126 | 5/1975 | McKenna, Jr. | 524/357 |
| 4,022,742 | 5/1977 | Yoshimura et al. | 524/357 X |
| 4,102,839 | 7/1978 | Crochemore et al. | 524/357 X |
| 4,751,261 | 6/1988 | Miyata et al. | 524/357 X |

*Primary Examiner*—Judy M. Reddick
*Attorney, Agent, or Firm*—Sughrue, Mion, Zinn, Macpeak & Seas

[57] ABSTRACT

A coating solution for forming a composite metal oxide film containing: (A) at least one member selected from the group consisting of a reaction product, a partial hydrolyzate of the reaction product, and a partial acylated product of the reaction product wherein the reaction product is obtained by a reaction between at least one compound containing a carbonyl group and at least one metal compound; (B) a polyhydric alcohol compound; and (C) at least one member selected from the group consisting of a metal carboxylate compound; a metal nitrate compound; and a metal nitrite compound, which coating solution may also contain an alcohol-soluble polymer. The present invention is also directed to a process of making the same.

14 Claims, No Drawings

COATING SOLUTION FOR FORMING COMPOSITE METAL OXIDE FILM AND PROCESS FOR MAKING SAME

This is a divisional of application Ser. No. 08/155,150 filed on Nov. 22, 1993, now U.S. Pat. No. 5,508,332, which is a divisional of application Ser. No. 08/035,711 filed on Mar. 23, 1993 now U.S. Pat. No. 5,393,907.

FIELD OF THE INVENTION

The present invention relates to a coating solution for forming a composite metal oxide film; more particularly, the present invention relates to a coating solution that has high storage stability and which is capable of forming an adequately thick ferroelectric film.

BACKGROUND OF THE INVENTION

Composite metal oxides such as $PbTiO_3$–$PbZrO_3$, $PbTiO_3$, $PbTiO_3$–$PbZrO_3$–$La_2O_3$ and $LiNbO_3$ are currently used to form ferroelectric films. Such ferroelectric films display piezoelectricity, pyroelectricity, electrostriction and electrooptic effects. Taking advantage of these effects, ferroelectric films are extensively used in ultrasonic cleaning, or as vibrating transducers in phonograph pickups, communications filters, or in sound wave delay circuits, high voltage generating transformers or as electronics devices such as infrared sensors. The films are also used in ignition devices or as various electrooptic materials.

To form a ferroelectric film on a substrate, a solution containing a compound of Pb, Zr, Ti or some other suitable element is coated on the substrate and the resulting coat is dried and fired. This method is commonly employed for the various advantages it offers, such as the ease of operation and the possibility of forming a ferroelectric film on a substrate having a complex shape.

The compounds of Pb, Zr, Ti, etc., contained in the coating solutions conventionally used to form ferroelectric films, are usually present in the form of alkoxides; however, such alkoxide compounds are prone to undergo hydrolysis and the coating solution prepared using them does not have high storage stability since precipitates are likely to occur in that solution.

In order to solve these problems, it has been proposed by JP-A-61-97159 (the term "JP-A" as used herein means an "unexamined published Japanese patent application") that the alkoxy group in an alkoxide compound be partly replaced with a β-diketone group. In addition, a coating solution that will experience less formation of precipitates has been proposed in JP-A-65-6335 where the use of a solution comprising a mixture of a lead alkoxide or a lead salt, a zirconium alkoxide, a titanium alkoxide, ethanolamine and an alcohol are disclosed. However, none of these coating solutions have practically acceptable levels of storage stability and it is strongly desired to develop a coating solution having better storage stability. Furthermore, the thickness of ferroelectric films that can be formed by a single application of the heretofore known coating solutions is not greater than about 100 nm and, therefore, in order to attain a practically acceptable film thickness, several coats must be applied in superposition which only adds to the complexity of the coating process.

The present inventors conducted intensive studies with a view to providing a highly practical coating solution for forming a composite metal oxide film capable of working as a ferroelectric film, which coating solution has better storage stability than other versions and which could produce practically thick films by a single application. As a result, the inventors found that the stated objects could be attained by preparing a coating solution from a combination particular compounds.

SUMMARY OF THE INVENTION

The present invention provides a coating solution for forming a composite metal oxide film comprising:

(A) at least one member selected from among the group consisting of a reaction product, a partial hydrolyzate of the reaction product, and a partial acylated product of the reaction product wherein the reaction product is obtained by a reaction between at least one compound containing a carbonyl group and at least one metal compound represented by formula (I):

$$M_1A_n \qquad (I)$$

wherein $M_1$ is Ti, Zr, Nb, Hf or Ta; A is —OR or a halogen atom, R is a saturated or unsaturated hydrocarbon having 1–6 carbon atoms; and n is an integer of 2–5;

(B) a polyhydric alcohol compound; and (C) at least one member selected from the group consisting of formulas (II), (III) and (IV); wherein, formula (II) is a metal carboxylate compound represented by:

$$M_2(OCOR)_m \qquad (II)$$

wherein $M_2$ is Pb, Sr, Ba, Mg, Zn, La, Y or Li; R is a saturated or unsaturated hydrocarbon having 1–6 carbon atoms; and m is an integer of 1–4;

formula (III) is a metal nitrate compound represented by:

$$M_2(NO_3)_m \qquad (III)$$

wherein $M_2$ is Pb, Sr, Ba, Mg, Zn, La, Y or Li; and m is an integer of 1–4 ; and formula (IV) is a metal nitrite compound represented by:

$$M_3(NO_2)_l \qquad (IV)$$

wherein $M_3$ is Sr, Ba or Li; and l is an integer of 1 or 2.

The present invention also provides a process for producing a coating solution for forming a composite metal oxide film comprising the steps of:

reacting component (A) with component (B) and subsequently incorporating component (C); wherein, component (A) is at least one member selected from the group consisting of a reaction product, a partial hydrolyzate of the reaction product, and a partial acylated product of the reaction product wherein the reaction product obtained by a reaction between at least one compound containing a carbonyl group compound and at least one metal represented by formula (I):

$$M_1A_n \qquad (I)$$

wherein $M_1$ is Ti, Zr, Nb, Hf or Ta; A is —OR or a halogen atom, R is a saturated or unsaturated hydrocarbon having 1–6 carbon atoms; and n is an integer of 2–5, component (B) is a polyhydric alcohol compound, and component (C) is at least one metal compound selected from the group consisting of a metal carboxylate compound, a metal nitrate compound and a metal nitrite compound.

Also, the present invention provides a coating solution for forming a composite metal oxide film and a process for the same as above which further comprises an alcohol-soluble polymer as component (D).

DETAILED DESCRIPTION OF THE INVENTION

The present invention is described in detail below.

Component (A), to be used in the coating solution of the present invention, is at least one member selected from the reaction product between at least one compound containing a carbonyl group and a metal compound represented by formula (I) set forth hereinabove, a partial hydrolyzate of the reaction product, and a partial acylated product of the reaction product. Two examples of the metal compound represented by the general formula (I) are a metal alkoxide compound and a metal halide compound. Examples of the metal alkoxide compounds to be used in the present invention include $Ti(OCH_3)_4$, $Ti(OC_2H_5)_4$, $Ti(OC_3H_7)_4$, $Ti(OC_4H_9)_4$, $Ti(OC_5H_{11})_4$, $Ti(OC_6H_{13})_4$, $Zr(OC_2H_5)_4$, $Zr(OC_3H_7)_4$, $Zr(OC_4H_9)_4$, $Zr(OC_5H_{11})_4$, $Zr(OC_6H_{13})_4$, $Nb(OCH_3)_4$, $Nb(OC_2H_5)_4$, $Nb(OC_3H_9)_4$, $Nb(OC_4H_9)_4$, $Nb(OC_5H_{11})_4$, $Nb(OC_6H_{13})_4$, $Ta(OCH_3)_4$, $Ta(OC_2H_5)_4$, $Ta(OC_3H_7)_4$, $Ta(OC_4H_9)_4$, $Ta(OC_5H_{11})_4$, $Ta(OC_6H_{13})_4$, $Hf(OCH_3)_4$, $Hf(OC_2H_5)_4$, $Hf(OC_3H_7)_4$, $Hf(OC_4H_9)_4$, $Hf(OC_5H_{11})_4$ and $Hf(OC_6H_{13})_4$. These metal alkoxide compounds may be used either individually or in admixture.

Examples of the metal halide compounds to be used in the present invention include $TiCl_4$, $TiBr_4$, $TiI_4$, $ZrCl_4$, $ZrBr_4$, $ZrI_4$, $NbCl_{14}$, $NbBr_4$, $NbI_4$, $TaCl_4$, $TaBr_4$, $TaI_4$, $HfCl_4$ and $HfBr_4$. These metal halide compounds may be used either individually or in admixture.

Examples of the compounds containing a carbonyl group to be used in the present invention include β-diketones and keto acid esters, such as acetylacetone, trifluoroacetylacetone, hexafluoroacetylacetone, benzoylacetone, benzoyltrifluoroacetone, dibenzoylmethane, methyl acetoacetate, ethyl acetoacetate and butyl acetoacetate. These compounds may be used either individually or in admixture. Preferred compounds containing a carbonyl group are methyl acetoacetate, ethyl acetoacetate and butyl acetoacetate.

The reaction product of at least one kind selected from the metal compounds shown by general formula (I), which is the component (A), and a compound containing a carbonyl group is a chelate compound formed from the metal compound shown by general formula (I) and the compound containing a carbonyl group. As the reaction condition for preparing the chelate compound, it is preferred to react from 1 to 6 mols of the compound containing a carbonyl group" and 1 mol of the foregoing metal compound shown by general formula (I). Also, the reaction may be carried out by a method of simultaneously adding the metal compound shown by general formula (I) and the compound containing a carbonyl group into an organic solvent, a method of adding dropwise the compound containing a carbonyl group to a solution obtained by dissolving the metal compound shown by general formula (I) in an organic solvent, etc.

The partial hydrolysis product of the reaction product of at least one kind selected from the metal compounds shown by general formula (I) and the compound containing a carbonyl group can be obtained by adding water to the reaction product of the metal compound shown by general formula (I) and the compound containing a carbonyl group or by the reaction of the reaction product and water formed in the solution of the reaction mixture. In this case, an acid such as hydrochloric acid, nitric acid, sulfuric acid, etc., may be added to the reaction system. In addition, since the partial hydrolysis product formed is an unstable material, the product becomes a condenstion product by a dehydration reaction. The product in the hydrolysis reaction is the reaction product of the metal compound shown by general formula (I) and the compound containing a carbonyl group a part of the alkoxy group or the halogen group of which remains, that is, the partial hydrolysis product. The preferred partial hydrolysis product can be obtained by adding water to the reaction product in an amount of from 0.5 to 8 mols to 1 mol of the metal compound shown by general formula (I).

Also, the partial acylation product of the reaction product of at least one kind of the metal compounds shown by general formula (I) and the compound containing a carbonyl group can be obtained by reacting the reaction product of the metal compound shown by general. formula (I) and the compound containing a carbonyl group with a carboxylic acid such as glacial acetic acid, acetic anhydride, acetic acid, propionic acid, etc. The product of the partial acylation is the reaction product of the metal compound shown by general formula (I) and the compound containing a carbonyl group a part of the alkoxy group or the halogen group of which remains, that is, a partial acylation product. The preferred acrylation product can be obtained by adding the carboxylic acid to the reaction product in an amount of from 0.5 to 8 mols to 1 mol of the metal compound shown by general formula (I).

The polyhydric alcohol compound used as component (B) in the coating solution of the present invention is an essential component for the purpose of enhancing the solubility of component (C) and the storage stability of the coating solution. Examples of the polyhydric alcohols to be used in the present invention include ethylene glycol, triethylene glycol, propylene glycol, dipropylene glycol, butane diol, hexylene glycol, octylene glycol, glycerin, glyceryl. monoacetate, glyceryl monobutyrate, trimethylolpropane, glyceryl monoacrylate and glyceryl monomethacrylate. These polyhydric alcohol compounds may be used either individually or in admixture. Particularly preferred polyhydric alcohol compounds are propylene glycol, glyceryl monoacetate, glyceryl monobutyrate, glyceryl monoacrylate and glyceryl monomethacrylate.

The polyhydric alcohol compound to be used as component (B) in the present invention is preferably reacted with compound (A). By using the product of the reaction between 1 mole of the metal compound as component (A) and 1–6 moles of the polyhydric alcohol, a coating solution having excellent storage stability can be prepared. The identity of the reaction product can be verified by the change that occurs in the color of the reaction solution formed by incorporating component (B) into component (A). With respect to function, component (B) is completely different from the organic solvents listed below. That is, component (B) is generally used for the purpose of enhancing the solubility of component (C) and component (B) is generally used for the purpose of insuring the necessary film-forming property of the coating solution.

It is considered that in the reaction of the polyhydric alcohol compound of the component (B) and the foregoing component (A), there occurs the ester interchange reaction of the alkoxy group of the component (A) and the polyhydric alcohol compound of the component (B) or the substitution reaction of the halogen group of the component (A) and the polyhydric alcohol compound of the component (B).

As component (C) of the coating solution of the present invention, at least one member selected from among a metal carboxylate, metal nitrate and metal nitrite compound represented by formulas (II), (III) and (IV), respectively, as set forth hereinabove, is/are used. Examples of the metal carboxylate compounds to be used in the present invention include $Ba(CH_3COO)_2nH_2O$, $La(CH_3COO)_3nH_2O$, $Pb(CH_3COO)_2nH_2O$, $Li(CH_3COO)nH_2O$, $Zn(CH_3COO)_2nH_2O$, $Sr(CH_3COO)_2nH_2O$, $Y(CH_3COO)_3nH_2O$ and $Mg(CH_3COO)_2nH_2O$. Examples of the metal nitrate compounds to be used in the present invention include $Ba(NO_3)_2nH_2O$, $La(NO_3)_3nH_2O$, $Pb(NO_3)_2nH_2O$, $Li(NO_3)nH_2O$, $Mg(NO_3)_2nH_2O$, $Sr(NO_3)_2nH_2O$, $Zn(NO_3)_2nH_2O$ and $Y(NO_3)_3nH_2O$. Examples of the metal nitrite compounds to be used in the present invention include $Sr(NO_2)_2nH_2O$, $Ba(NO_2)_2nH_2O$ and $Li(NO_2)nH_2O$. These compounds may be used either individually or in admixture.

The coating solution of the present invention contains the three essential components (A), (B) and (C) described above. If desired, an alcohol-soluble polymer may be incorporated as component (D) and the resulting coating solution is characterized by marked improvement in the ability to form thick films.

While any polymers that are soluble in alcohol can be used as component (D) without particular limitation, preferred polymers are those which have hydroxyl groups in their structure. Examples of the alcohol-soluble polymers to be used in the present invention include polyvinyl alcohol in which vinyl acetate is partially saponified, formal resins, butyral resins, polyglycerin, as well as homo- and copolymers of 2-hydroxymethyl acrylate, 2-hydroxymethyl methacrylate, 2-hydroxyethyl acrylate, 2-hydroxyethyl methacrylate, 2-hydroxypropyl acrylate, 2-hydroxypropyl methacrylate, 2-hydroxybutyl acrylate and 2-hydroxybutyl methacrylate.

The coating solution of the present invention contains components (A), (B) and (C), with component (D) being incorporated optionally. To improve the film-forming ability of the coating solution, the respective components are preferably used as dissolved in organic solvents. Examples of organic solvents that can be used for this purpose include: methyl alcohol, ethyl alcohol, isopropyl alcohol, n-propyl alcohol, n-butyl alcohol, ethylene glycol, propylene glycol, butylene glycol, hexylene glycol, octylene glycol, diethylene glycol, dipropylene glycol, dihexylene glycol, ethylene glycol monomethyl ether, ethylene glycol monoethyl ether, ethylene glycol monobutyl ether, ethylene glycol monopropyl ether, ethylene glycol monophenyl ether, ethylene glycol monobenzyl ether, propylene glycol monomethyl ether, propylene glycol monoethyl ether, propylene glycol monobutyl ether, ethylene glycol dimethyl ether, ethylene glycol diethyl ether, ethylene glycol dibutyl ether, ethylene glycol dipropyl ether, ethylene. glycol dibenzyl ether, ethylene glycol methyl ethyl diether, propylene glycol dimethyl ether, propylene glycol diethyl ether, propylene glycol dibutyl ether, methyl carbitol, ethyl carbitol, butyl carbitol, phenyl carbitol, benzyl carbitol, dimethyl carbitol, diethyl carbitol, dibutyl carbitol, diphenyl carbitol, dibenzyl carbitol, methyl ethyl carbitol, dipropylene glycol dimethyl ether, dipropylene glycol diethyl ether and dipropylene glycol dibutyl ether. These organic solvents may be used either individually or in admixture.

The process for producing the coating solution of the present invention is described below. The coating solution of the present invention is prepared by dissolving the essential components (A), (B) and (C), optionally component (D), too, in an organic solvent. When producing the coating solution, it is important that the reaction product of component (A) be first reacted with the polyhydric alcohol of component (B) and then at least one member of component (C) selected from among the metal carboxylate compound (II), the metal nitrate compound (III) and the metal nitrite compound (IV) should be added to the reaction product thus obtained. If this order of addition is not observed, it is impossible to prepare a coating solution that has good solubility and high storage stability. As already mentioned, component (D) is added to a coating solution prepared from the essential components (A), (B) and (C).

The respective components are incorporated in the following proportions. The polyhydric alcohol compound as. component (B) is incorporated in an amount of at least 1 mole, preferably 1–6 moles, per mole of the metal compound used to form component (A); component (C) selected from among various metal compounds is incorporated in an amount of 0.5–5 moles, preferably 0.8–3 moles, per mole of the metal compound used to form component (A). If the components are added in amounts that are outside the ranges specified above, a coating solution having good storage stability cannot be prepared. The alcohol-soluble polymer of component (D), when used, is incorporated in an amount of 1–100 parts by weight, preferably 3–40 parts by weight, per 100 parts by weight of the solids content of the coating solution prepared from components (A), (B) and (C). If component (D) is added in amounts that are outside the range of 1–100 parts by weight, a thick and highly uniform film cannot be formed.

The coating solution of the present invention may be applied to various kinds of substrates including those which are produced by sintering the particles of plastics, glass, ceramics, metal nitrides and metal carbonates, as well as metal and semiconductor substrates. Upon subsequent heating, composite metal oxide films can be produced as highly uniform ferroelectric films. Any conventional coating method may be employed as selected from among the dip-and-lift method, spraying, spin coating, brush coating, roll coating and printing. Examples of the heating means include hot plates, hot air, a burner, infrared radiation, laser and RF current. The heating temperature must be at least 250° C., preferably at least 350° C., for the purpose of forming chemically stable films; however, it is subject to limitation by various factors such as the constituent materials of a specific substrate and, hence, appropriate values should be selected from the temperature ranges which the substrate can withstand.

Being prepared from the combination of the essential components (A), (B) and (C), the coating solution of the present invention has far better storage stability than the conventional versions and a ferroelectric film of desired characteristics can be readily formed by applying the solution. Furthermore, a thick film can be formed by a single application of the coating solution and this is of great benefit from the viewpoint of practical applications. If component (D) is added to the coating solution prepared from the combination of components (A), (B) and (C), a coating solution is produced that has better adaptability for producing a thick film by a single application and which, as a result, has even greater value for practical purposes.

The present invention is now illustrated in greater detail by reference to the following examples, which are not to be construed as limiting the present invention in any way.

EXAMPLE 1

Tetrapropoxytitanium (28.4 g, 0.1 mole) was mixed with methyl acetoacetate (23.2 g, 0.2 mole) and the mixture was stirred at 80° C. for 30 min. to initiate reaction. Then, glacial acetic acid (6.1 g, 0.1 mole) was added and the reaction was continued at 80° C. for 30 min. Thereafter, the reaction system was returned to room temperature, followed by addition of glyceryl monoacetate (13.4 g, 0.1 mole), and the reaction was continued at 80° C. for 30 min. Thereafter, the reaction system was returned to room temperature, followed by addition of ethylene glycol monomethyl ether (50 g) and strontium acetate (21.4 g, 0.1 mole), and the system was heated to 40° C. so that all ingredients were mixed together and dissolved to give a coating solution.

The coating solution was spin-coated onto a silicon wafer at 3,000 rpm for 30 sec; the wafer was dried at 60° C for 20 min and fired at 400° C. for 30 min. in air to produce a clear uniform film of $SrTiO_3$ in a thickness of about 100 nm. Upon standing at room temperature for 3 months, the coating solution showed no sign of precipitation of impurities or the like, nor was any change observed in its characteristics.

EXAMPLE 2

Tetrapropoxyzirconium (29.48 g, 0.09 mole) was mixed with tetrabutoxytitanium (3.40 g, 0.01 mole) under stirring at 80° C. for 30 min.; thereafter, ethyl acetoacetate (26 g, 0.2 mole) was added and the mixture was stirred at 80° C. for an additional 30 min. to initiate reaction, followed by addition. of a mixture of water (1.8 g, 0.1 mole), conc. HCl (5 µl ) and ethylene glycol monomethyl ether (10 g). The reaction was continued at 60° C. for 60 min., followed by addition of propylene glycol (15.2 g, 0.2 mole). The mixture was heated at 60° C. for 30 min. and, thereafter, lead acetate (37.9 g) was added and the system was heated at 50°–70° C. so that all ingredients dissolved to give a coating solution.

The coating solution was spin-coated onto a silicon wafer at 4,000 rpm for 30 sec.; the wafer was dried at 80° C. for 15 min. and fired at 500° C. for 40 min. in air to produce a clear uniform film in a thickness of about 200 nm. Upon standing at room temperature for 3 months, the coating solution showed no sign of precipitation of impurities or the like, nor was any change observed in its characteristics.

EXAMPLE 3

Tetrapropoxyzirconium (29.48 g, 0.09 mole) was mixed with tetrabutoxytitanium (3.40 g, 0.01 mole) under stirring at 80° C. for 30 min.; thereafter, ethyl acetoacetate (26 g, 0.2 mole) was added and the mixture was stirred at 80° C. for an additional 30 min. to initiate reaction, followed by addition of propylene glycol (15.2 g, 0.2 mole). The mixture was heated at 60° C. for 30 min., followed by addition of lead acetate (37.9 g). The mixture was heated at 50°–70° C. so that all ingredients dissolved to give a coating solution.

The coating solution was spin-coated onto a silicon wafer at 4,000 rpm for 30 sec; the wafer was dried at 80° C. for 15 min. and fired at 500° C. for 40 min. in air to produce a clear uniform film in a thickness of about 150 nm. Upon standing at room temperature for 3 months, the coating solution showed no sign of precipitation of impurities or the like, nor was any change observed in its characteristics.

EXAMPLE 4

To 10 g of the coating solution prepared in Example 3, 15 g of 20 wt % poly2-hydroxypropyl methacrylate, as dissolved in ethylene glycol monomethyl ether, was added to prepare a coating solution. Using this coating solution, the procedure of Example 3 was repeated to form a clear uniform film in a thickness of about 500 nm. Upon standing at room temperature for 3 months, the coating solution showed no sign of precipitation of impurities or the like, nor was any change observed in its characteristics.

EXAMPLE 5

To 10 g of the coating solution prepared in Example 3, 10 g of 20 wt % butyral resin (3000-2 of Denki Kagaku Kogyo K.K.) as dissolved in ethylene glycol monomethyl ether was added to prepare a coating solution. Using this coating solution, the procedure of Example 3 was repeated to form a clear uniform film in a thickness of about 500 nm. Upon standing at room temperature for 3 months, the coating solution showed no sign of precipitation of impurities or the like, nor was any change observed in its characteristics.

EXAMPLE 6

Tetrapropoxyzirconium (170.40 g, 0.52 mole) was mixed with tetrabutoxytitanium (163.37 g, 0.48 mole) under stirring at 80° C. for 30 min. To 13.2 g of the resulting solution, ethyl acetoacetate (10.4 g, 0.08 mole) was added and the mixture was stirred at 100° C. for an additional 30 min., followed by addition of a mixture of water (0.72 g, 0.04 mole), conc. HCl (10 µl) and ethylene glycol monomethyl ether (4 g). The reaction was continued at 80° C. for 30 min., followed by addition of propylene glycol (6 g, 0.08 mole). The mixture was heated at 80° C. for 30 min. and, thereafter, lead acetate (15.7 g) was added and the system was heated at 50°–70° C. so that all ingredients dissolved to form a solution. Then, 10 g of 36 wt % poly2-hydroxypropyl methacrylate, as dissolved in ethylene glycol monomethyl ether, was added thereby giving a coating solution.

The coating solution was spin-coated onto a silicon wafer at 4,000 rpm for 30 sec; the wafer was dried at 80° C. for 15 min. and fired at 500° C. for 40 min. in air to produce a clear uniform film in a thickness of about 500 nm. Upon standing at room temperature for 3 months, the coating solution showed no sign of precipitation of impurities or the like, nor was any change observed in its characteristics.

EXAMPLE 7

After mixing 19.18 g (0.05 mol) of tetrabutoxyzirconium and 17.02 g (0.05 mol) of tetrabutoxytitanium with stirring at 80° C. for 30 minutes, 11.6 g (0.1 mol) of methyl acetoacetate and 13.0 g (0.1 mol) of ethyl acetoacetate were added to the mixture and the reaction was carried out by further stirring at 80° C. for 30 minutes. Thereafter, when the temperature of the reaction mixture was lowered to room temperature, 15.2 g (0.2 mol) of propylene glycol was added thereto and after heating again the reaction mixture to 60° C. for 30 minutes with stirring, 30.3 g (0.08 mol) of lead acetate was added thereto followed by heating to a temperature of from 50° C. to 70° C. to dissolve lead acetate. Thereafter, 20 g of ethylene glycol monomethyl ether was added to the mixture with stirring and the resultant mixture was allowed to cool to room temperature. Then, a liquid previously prepared by mixing 8.7 g (0.02 mol)of lanthanum nitrate, 7.0 g of methyl acetoacetate, and 10 g of ethylene glycol monomethyl ether was mixed with the reaction mixture thus obtained with stirring to provide a coating liquid.

Then, the coating liquid was coated on a silicon wafer by a spin coating method at 4,000 r.p.m. for 30 seconds and after drying the coated liquid at 80° C. for 10 minutes, the

What is claimed is:

1. A coating composition solution for forming a composite metal oxide film comprising:

(A) at least one member selected from the group consisting of a reaction product, a partial hydrolyzate of said reaction product, and a partial acylated product of said reaction product, wherein said reaction product is obtained by a reaction between at least one compound containing a carbonyl group and at least one metal compound represented by formula (I):

$$M_1A_n \qquad (I)$$

wherein $M_1$ is Ti, Zr, Nb, Hf or Ta; A is —OR or a halogen atom, R is a saturated or unsaturated hydrocarbon having 1–6 carbon atoms; and n is an integer of 2–5, (B) a polyhydric alcohol compound, (C) at least one compound selected from the group consisting of formulas (II), (III) and (IV); wherein, formula (II) is a metal carboxylate compound represented by:

$$M_2(OCOR)_m \qquad (II)$$

wherein $M_2$ is Pb, Sr, Ba, Mg, Zn, La, Y or Li; R is a saturated or unsaturated hydrocarbon having 1–6 carbon atoms; and m is an integer of 1–4;

formula (III) is a metal nitrate compound represented by:

$$M_2(NO_3)_m \qquad (III)$$

wherein $M_2$ is Pb, Sr, Ba, Mg, Zn, La, Y or Li; and m is an integer of 1–4; and formula (IV) is a metal nitrite compound represented by:

$$[M_3(NO_2)]M_3(NO_2)_l \qquad (IV)$$

wherein $M_3$ is Sr, Ba or Li; and l is an integer of 1 or 2, and (D) an alcohol soluble polymer.

2. A coating solution for forming a composite metal oxide film according to claim 1, wherein the at least one compound containing a carbonyl qroup is at least one compound selected from the group consisting of methyl acetoacetate, ethyl acetoacetate, and butyl acetoacetate.

3. A coating solution for forming a composite metal oxide film according claim 1, wherein the polyhydric alcohol compound is at least one member selected from the group consisting of propylene glycol, glyceryl monoacetate, glyceryl monobutyrate, glyceryl monoacrylate and glyceryl monomethacrylate.

4. A coating solution for forming a composite metal oxide film according to claim 1, wherein the alcohol-soluble polymer is a polymer containing hydroxyl groups.

5. A coating solution for forming a composite metal oxide film according to claim 4, wherein the alcohol soluble polymer containing hydroxyl groups is at least one polymer selected from the group consisting of (a) a partially saponified polyvinyl acetate, (b) a formal resin, (c) a butyral resin, (d) polyglycerin, and (e) a polymerization product formed of at least one member selected from the group consisting of 2-hydroxymethyl acrylate, 2-hydroxymethyl methacrylate, 2-hydroxyethyl acrylate, 2-hydroxyethyl methacrylate, 2-hydroxypropyl acrylate, 2-hydroxypropyl methacrylate, 2-hydroxybutyl acrylate and 2-hydroxybutyl methacrylate.

6. A coating solution for forming a composite metal oxide film according to claim 1, wherein the at least one compound containing a carbonyl group is incorporated in an amount of 1–6 moles per mole of the at least one metal compound represented by formula (I).

7. A coating solution for forming a composite metal oxide film according to claim 1, wherein the polyhydric alcohol compound is incorporated in an amount of at least one mole per mole of the at least one metal compound represented by formula (I).

8. A coating solution for forming a composite metal oxide film according to claim 7, wherein the polyhydric alcohol compound is incorporated in an amount of 1–6 moles per mole of the at least one metal compound represented by formula (I).

9. A coating solution for forming a composite metal oxide film according to claim 1, wherein the at least one member selected from the group consisting of formulas (II), (III), and (IV) is incorporated in an amount of 0.5–5 moles per mole of the at least one metal compound represented by formula (I).

10. A coating solution for forming a composite metal oxide film according to claim 9, wherein the at least one member selected from the group consisting of formulas (II), (III) and (IV) is incorporated in an amount of 0.8–3 moles per mole of the at least one metal compound represented by formula (I).

11. A coating solution for forming a composite metal oxide film according to claim 1, wherein the alcohol-soluble polymer is incorporated in an amount of 1–100 parts by weight per 100 parts by weight of the solids content of a coating solution prepared from components (A), (B) and (C).

12. A coating solution for forming a composite metal oxide film according to claim 11, wherein the alcohol-soluble polymer is incorporated in an amount of 3–40 parts by weight per 100 parts by weight of solids content of a coating solution prepared from components (A), (B) and (C).

13. A coating solution for forming a composite metal oxide film according to claim 1, wherein the at least one compound containing a carbonyl group is at least one compound selected from the group consisting of a β-diketone and a keto acid ester.

14. A coating solution for forming a composite metal oxide film according to claim 1, wherein the coating solution is dissolved in at least one organic solvent.

* * * * *